United States Patent [19]

Synoradzki et al.

[11] Patent Number: 4,795,820

[45] Date of Patent: Jan. 3, 1989

[54] METHOD OF MANUFACTURING TINORGANIC COMPOUNDS AND STABILIZERS

[75] Inventors: Ludwik Synoradzki; Jacek Lasota; Boguslaw Zielinski; Andrzej Kasprzak; Maciej Uninski; Bogdan Siwanowicz; Tomasz Dluzniewski; Andrzej Gieysztor; Roman Zadrozny; Andrzej Smyk; Pazgan Andrzej, all of Warsaw; Irena Dobosz, Sochaczew; Teresa Brzozowska-Janiak, Sochaczew; Zdzislaw Szawlowski, Sochaczew; Ireneusz Dusinski, Sochaczew, all of Poland

[73] Assignees: Politchnika Warszawska; Warszawa Zaklady Tworzyw Sztucznych "Boryszew-Erg", both of Sochaczew, Poland

[21] Appl. No.: 907,095

[22] Filed: Sep. 12, 1986

[30] Foreign Application Priority Data

Sep. 25, 1985 [PL] Poland .................................. 255511

[51] Int. Cl.$^4$ .............................................. C07F 7/22

[52] U.S. Cl. ...................... 556/105; 556/88; 556/89; 556/90; 556/91; 556/92; 556/94; 556/93

[58] Field of Search ...................... 556/91, 92, 94, 88, 556/89, 90, 105

[56] References Cited

U.S. PATENT DOCUMENTS

| | | | |
|---|---|---|---|
| 4,080,362 | 3/1978 | Hutton et al. | 556/92 X |
| 4,080,363 | 3/1978 | Hutton et al. | 556/92 X |
| 4,134,878 | 1/1979 | Burley et al. | 556/92 X |
| 4,237,043 | 12/1980 | Korbanka et al. | 556/92 X |
| 4,292,252 | 9/1981 | Collins et al. | 556/91 X |
| 4,324,737 | 4/1982 | Fouré | 556/91 X |
| 4,554,368 | 11/1985 | Maul et al. | 556/91 X |

FOREIGN PATENT DOCUMENTS

2607178 10/1976 Fed. Rep. of Germany .
1487879 10/1977 United Kingdom .

*Primary Examiner*—Paul F. Shaver
*Attorney, Agent, or Firm*—Ladas & Parry

[57] ABSTRACT

A method of manufacture of tinorganic compounds.

15 Claims, 1 Drawing Sheet

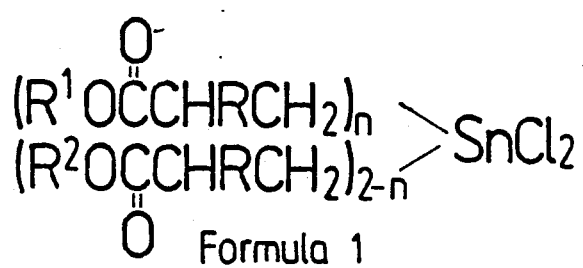
Formula 1
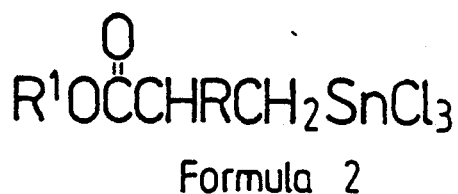
Formula 2
Formula 3
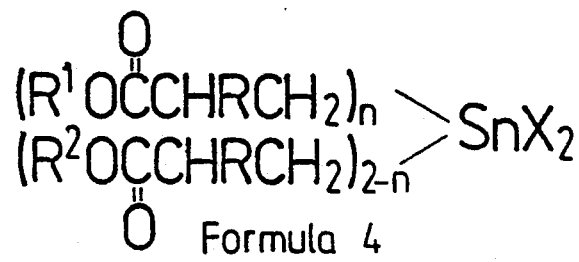
Formula 4
Formula 5
Formula 6

METHOD OF MANUFACTURING TINORGANIC COMPOUNDS AND STABILIZERS

The subject of the invention is the method of manufacturing tinorganic compounds with general formula 1 and/or 2 and/or 3, where R is a hydrogen atom or alkyl group with 1-18 carbon atoms, $R^1$ is an alkyl group with 1-4 carbon atoms, $R^2$ is an alkyl group with 1-18 carbon atoms, "n" value is 0, 1 or 2 and the alkyle groups in substituents $R^1OC/O/CHRCH_2$ and $R^2OC/O/CHRCH_2$ may be the same or different. These compounds are used for obtaining heat stabilizers of polymers, particularly PVC, and as fungicides.

The scope of the invention includes also the method of manufacturing tinorganic stabilizers, which form compounds with general formula 4 and/or 5 and/or 6, where "n" value is 0, 1 or 2, R is a hydrogen atom or an alkyl group with 1-18 carbon atoms, $R^1$ is an alkyl group with 1-4 carbon atoms, $R^2$ is an alkyl group with 1-18 carbon atoms, X is a group with formula $S/CH_2/_mC/O/OR^2$, $SR^2$, $OC/O/R^2$ or $OC/O/CH=CHC/O/OR^2$, where "m" value is 1 or 2, $R^2$ has the above specified meaning, and alkyl groups in substituents $R^1OC/O/CHRCH_2$ and $R^2OC/O/CHRCH_2$ may be the same or different. Such compounds, preferably in the form of mixture, are used in the plastics industry as heat stabilizers of polymers, particularly PVC.

Moreover, the subject of the invention comprises also compounds with general formula 1, where "n" value is 1, R, $R^1$ and $R^2$ have the above specified meaning, and alkyl groups in substituents $R^1OC/O/CHRCH_2$ and $R^2OC/O/CHRCH_2$ bounded with tin are different, and compounds with general formula 4, where "n" value is 1, R, $R^1$, $R^2$ and X have the above specified meaning and the alkyl groups in substituents $R^1OC/O/CHRCH_2$ and $R^2OC/O/CHRCH_2$ bounded with tin are different. These compounds are new and have not yet been described in literature.

West German Pat. No. 2607178 describes a method of manufacturing tinorganic compounds in which alkyl ester of α-unsaturated carboxylic, metallic tin and hydrogen chloride are put into reaction, which results in creating a mixture of estertins with formula $R^2OC/O/CH_2CH_2SnCl_3$ and $[R^2OC/O/CH_2CH_2]_2SnCl_2$. This mixture is put into reaction with monocarboxylic acids comprising 6-18 carbon atoms in a molecule, partial esters of dicarboxylic unsaturated acids, thiols and thioesters. The product of this reaction is a stabilizer in form of mono- and diester tinorganic derivatives, in which the ester radical is always the same and corresponding with the initial ester.

The method as per the invention is such, that the alkyl ester of α-unsaturated carboxylic acid with the general formula $R^1OC/O/CR=CH_2$, where R and $R^1$ have the above specified meaning, are put simultaneously into reaction with metallic tin, an alcohol with a general formula $R^2OH$, where $R^2$ has the above specified meaning and hydrogen chloride, possibly in an organic solvent. The reaction effects in single tinorganic compounds with general formulas 1, 2 or 3, or mixture of these compounds. After prior distilling off lower boiling alcohols and the solvent, the obtained compounds with general formulas 1 and/or 2 and/or 3, where R, $R^1$, $R^2$ and "n" have the above specified meaning, are put into reaction with a compound with a general formula $HS/CH_2/_mC/O/OR^2$, where $R^2$ and "m" have the above specified meaning, a compound with a general formula $HSR^2$, where $R^2$ has the above specified meaning, a compound with a general formula $HOC/O/R^2$, where $R^2$ has the above specified meaning, or a compound with the general formula $HOC/O/CH=CHC/O/OR^2$, where $R^2$ has the above specified meaning, possibly in an organic solvent, preferably the one used at the previous stage and then, after possible removal of lower boiling alcohol and the solvent, compounds with the general formula 4, and/or 5, and/or 6 are obtained, in which R, $R^1$, $R^2$, X, "m" and "n" have the above specified meaning. The reaction may result in obtaining single tinorganic compounds or their mixture.

Formulas (FIGS.) 1 to 6 of the drawing depict compounds according to the invention.

During the first stage of this reaction simultaneous synthesis of estrochlorotins and transesterification with production of alcohol with general formula $R^1OH$ takes place. Preferably, the process should be executed in such a way that at atmospheric pressure the temperature should not exceed 60° C. During destilling off the alcohol and solvent from the reaction mixture, further transesterification takes place, producing a larger amount of $R^2$ alkyl groups in the mixture of products. The obtained mixture need not be separated into particular compounds and can be further processed to obtain the stabilizer.

The method as per the invention enables producing tinorganic compounds and stabilizers which are ester derivatives, in which alkyl groups situated in substituents $R^1OC/O/CHRCH_2$ and $R^2OC/O/CHRCH_2$ are different. The compound with the general formula 4 has a very advantageous effect on the properties of the stabilizer obtained by the method of the invention.

The method as per the invention ensures high yield of the product and considerable acceleration of the reaction.

It enables obtaining a high degree of reaction effectiveness and utilization of tin and ester, does not produce by products and the apparatus used for its execution is simple and uncomplicated. It may be applied at industrial scale.

The method of the invention is based on the transesterification reaction in direct synthesis from esters, alcohol, tin and hydrogen chloride. It allows for acceleration of the reaction and better utilization of the capacity of the apparatus. The subject of the invention is further explained in examples of manufacture:

Example I. 0.6 mole of methyl acrylate, 0.3 mole of powdered tin, 1.2 mole of n-butanol-1 where consecutively introduced into a 250 cu.cm. reactor, equipped with a mixer, a reflux condenser and a bubbler. During intensive mixing 0.9 mole of gas hydrogen chloride was added at a speed of 1.5 mole$_{HCl}$/mole$_{Sn}$/h. The reactor was surface cooled with water so that the temperature did not exceed 50° C. and after introducing of the assumed quantity of hydrogen chloride, the temperature was maintained for a further hour. The post-reaction mixture was warmed for an hour, at a boiling point, to the temperature of 70° C.–120° C., and at the same time 9.4 g of methanol was distilled off. Next, the excess of butanol was removed through vacuum distillation, and after filtering 108 g product with the following composition was obtained:

$CH_3OC/O/CH_2CH_2SnCl_3$-6%
$C_4H_9OC/O/CH_2CH_2SnCl_3$-26%
$[CH_3OC/O/CH_2CH_2]_2SnCl_2$-3%

[CH₃OC/O/CH₂CH₂][C₄H₉OC/O/CH₂CH₂]SnCl₂-34%

[C₄H₉OC/O/CH₂CH₂]₂SnCl₂-31% with a yield of 91%.

Example II. The reactor is in the same as that described in Example I. The consecutively introduced components were: 0.6 mole of methyl acrylate, 0.3 mole of tin powder, 1.65 mole n-butanol 1. During intensive mixing 0.9 mole of gas hydrogen chloride was added, at the speed of 1,0 mol$_{HCl}$/mol$_{Sn}$/h. The reactor was surface cooled with water, so that the temperature did not exceed 40° C. The obtained post-reaction mixture was warmed for an hour in the boiling condition to the temperature of 70° C.–120° C., sumultaneously distilling off 8.7 g of methanol. Next, the excess of butanol was removed through vacuum distillation and after filtering 105 g of a product with the following composition was obtained:

CH₃OC/O/CH₂CH₂SnCl₃-8%

C₄H₉OC/O/CH₂CH₂SnCl₃-21%

[CH₃OC/O/CH₂CH₂]₂SnCl₂-6%

[CH₃OC/O/CH₂CH₂][C₄H₉OC/O/CH₂CH₂]SnCl₂-38%

[C₄H₉OC/O/CH₂CH₂]₂SnCl₂-27% with the yield of 88%.

Example III. 0.6 mole of methyl acrylate, 0.3 mole of powdered tin, 3,0 mole of n-butanol-1 were consecutively introduced into a 250 cu.cm. reactor equipped with a mixer, a reflux condenser and a bubbler. During intensive mixing 0.9 mole of gas hydrogen chloride was added at a speed of 1.5 mole$_{HCl}$/moles$_{Sn}$/h. The reactor was surface cooled with water so that the temperature did not exceed 30° C. and after introduction of the assumed quantity of hydrogen chloride such temperature was maintained for a following hour. The post-reaction mixture was warmed for an hour in the boiling condition to the temperature of 70° C.–120 ° C., simultaneously distilling off 17.3 g of methanol. Next, the excess of butanol was removed through vacuum distillation and after filtering 121.2 g of a compound with a formula [C₄H₉OC/O/CH₂CH₂]₂SnCl₂ was obtained with the yield of 90%.

Example IV. 0.6 mole of methyl acrylate, 0.3 mole of powdered tin, 1.65 mole of n-butanol-1 were put consecutively into a 250 cu.cm. reactor, equipped with a mixer, a reflux condenser and a bubbler, together with 0.9 mole of gas hydrogen chloride, added at a speed of 1 mole$_{HCl}$/moles$_{Sn}$/h. In order to keep the temperature of reaction from rising above 40° C. during adding hydrogen chloride and intensive mixing, the reactor was surface cooled and then the temperature was maintained for an hour. The boiling post-reaction mixture was warmed for an hour to the temperature of 70° C. to 100° C., simultaneously distilling off 8.8 g of methanol. To the mixture of esterochlorotins obtained in this way butanol was added at standard temperature, together with 0.6 mole of 2-ethyl—hexyl thioglycolate, and next 10% solution of sodium hydroxide/1.0 mole NaOH/- was dropped in for one hour. After the said dropping in was ended, the reaction mixture was warmed for an hour at the temperature of 60° C., then the organic layer was separated from the water layer and washed twice with hot water. The excess of butanol was removed through vacuum distillation. After filtering away the remnants of solid substances, 187 g of a stabilizer with the following composition was obtained.

CH₃OC/O/CH₂CH₂Sn[SCH₂C/O/OC₈H₁₇]₃-4%

C₄H₉OC/O/CH₂CH₂Sn[SCH₂C/O/OC₈H₁₇]₃-15%

[CH₃OC/O/CH₂CH₂]₂Sn[SCH₂C/O/OC₈H₁₇]₂-9%

[CH₃OC/O/CH₂CH₂][C₄H₉OC/O/CH₂CH₂]Sn[SCH₂C/O/OC₈H₁₇]₂-42%

[C₄H₉OC/O/CH₂CH₂]₂Sn[SCH₂C/O/OC₈H₁₇]₂-30%

Degree of reaction efficiency of tin is 100% and degree of utilization of tin is 95%.

Example V. 0.6 mole of methyl acrylate, 0.3 mole of powdered tin, 1.2 mole of n-butanol-1 and 0.9 mole of gas hydrogen chloride were put consecutively into a reactor as in Example IV. The contents of the reactor was intensively surface cooled so that the temperature did not exceed 30° C. during introduction of hydrogen chloride and this temperature was then maintained for one hour. After filtering away 0.4 g of tin the boiling filtrate was warmed for 2 hours to the temperature of 70° C.–120° C., and simultaneously 8.7 g of methanol was distilled off. The excess of butanol was removed from the obtained mixture of estrochlorotins through vacuum distillation and light petrol was added, together with 0.6 mole of 2-ethyl—hexyl thioglycolate, then for one hour 8% solution of sodium bicarbonate/1.0 mole NaHCO₃/was dropped in, and the mixture mixed simultaneously. The product was warmed, separated and cleaned as in Example IV. The quantity of obtained stabilizer was 193 g, and its composition as follows:

CH₃OC/O/CH₂CH₂Sn[SCH₂C/O/OC₈H₁₇]₃-12%

C₄H₉OC/O/CH₂CH₂Sn[SCH₂C/O/OC₈H₁₇]₃-17%

[CH₃OC/O/CH₂CH₂]₂Sn[SCH₂C/O/OC₈H₁₇]₂-9%

[CH₃OC/O/CH₂CH₂][C₄H₉OC/O/CH₂CH₂]Sn[SCH₂C/O/OC₈H₁₇]₂-32%

[C₄H₉OC/O/CH₂CH₂]₂Sn[SCH₂C/O/OC₈H₁₇]₂-30%

The degree of reaction efficiency of tin is 99% and the degree of utilization of tin in the whole process is 95%.

We claim:

1. A process for manufacturing tinorganic compounds selected from the group consisting of

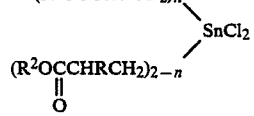 Formula 1

 Formula 2 and

 Formula 3 or mixtures thereof, wherein R is a hydrogen atom or an alkyl group with 1–18 carbon atoms, R¹ is an alkyl group with 1–4 carbon atoms, R² is an alkyl group with 1–18 carbon atoms and "n" is 0, 1 or 2, and wherein alkyl R¹ and R² groups may be the same or different comprising simultaneously reacting an alkyl ester of an α-unsaturated carboxylic acid of the formula R¹O-COCR=CH₂, wherein R and R¹ have the above specified meaning, with metallic tin and an alcohol of the formula R²OH wherein R² has the above specified means, and hydrogen chloride.

2. The process, as in claim 1 wherein R¹ and R² are different.

3. The process, as in claim 1 wherein the reaction of the alkyl ester of the unsaturated carboxylic acid is reacted with the metallic tin, and the alcohol of the formula $R^2OH$ in an organic solvent.

4. The process, as in claim 1 wherein a mixture of the 5 compounds is obtained.

5. The process, as in claim 1 wherein the alcohol of formula $R^2OH$ is n-butanol-1.

6. A process for manufacturing tinorganic stabilizers selected from the group consisting of $$\begin{array}{c} (R^1OCCHRCH_2)_n \\ \parallel \\ O \end{array} \diagdown SnX_2, \diagup \begin{array}{c} (R^2OCCHRCH_2)_{2-n} \\ \parallel \\ O \end{array}$$ Formula 4

$$\begin{array}{c} O \\ \parallel \\ R^1OCCHRCH_2SnX_3, \end{array}$$ and Formula 5

$$\begin{array}{c} O \\ \parallel \\ R^2OCCHRCH_2SnX_3 \end{array}$$ Formula 6 or mixture thereof, wherein "n" is 0, 1 or 2, R is a hydrogen atom or an alkyl group with 1–18 carbon atoms, $R^1$ is a 1–4 carbon atom alkyl group, $R^2$ is a 1–18 carbon atoms alkyl group, X is a group of the formula $SCH_{2m}COOR^2$, $SR^2$, $OCOR^2$ or $OCOCH=CH-COOOR^2$, and "m" is 1 or 2, $R^2$ has the above specified meaning, and wherein alkyl groups situated in substituents $R^1OCOCHRCH_2$ and $R^2OCOCHRCH_2$ may be the same or different, comprising reacting, simultaneously an ester of unsaturated carboxylic acid of the formula $R^1OCOCR=CH_2$, wherein R and R1 have the above specified meaning with metallic tin, and an alcohol of the formula $R^2OH$, wherein $R^2$ has the above specified meaning, and hydrogen chloride, and reacting the resulting compounds with a compound selected from the formula $$\begin{array}{c} (R^1OCCHRCH_2)_n \\ \parallel \\ O \end{array} \diagdown SnCl_2 \diagup \begin{array}{c} (R^2OCCHRCH_2)_{2-n} \\ \parallel \\ O \end{array}$$ Formula 1

$$\begin{array}{c} O \\ \parallel \\ R^1OCCHRCH_2SnCl_3 \end{array}$$ Formula 2 and $$\begin{array}{c} O \\ \parallel \\ R^2OCCHRCH_2SnCl_3 \end{array}$$ Formula 3 wherein R, $R^1$, $R^2$ and n have the above specified meaning, and reacting with a compound of the formula $HSCH_{2m}COOR^2$, wherein $R^2$ and "m" have the above specified meaning, a compound of the formula $HSR^2$, wherein $R^2$ has the above specified meaning, acompound of the formula $HOCOR^2$, wherein $R^2$ has the above specified meaning, or with a compound of the formula $HOCOCH=CHCOOR^2$, wherein $R^2$ has the above specified meaning wherein a compound selected from formula $$\begin{array}{c} (R^1OCCHRCH_2)_n \\ \parallel \\ O \end{array} \diagdown SnX_2 \diagup \begin{array}{c} (R^2OCCHRCH_2)_{2-n} \\ \parallel \\ O \end{array}$$ Formula 4

$$\begin{array}{c} O \\ \parallel \\ R^1OCCHRCH_2SnX_3 \end{array}$$ and Formula 5

$$\begin{array}{c} O \\ \parallel \\ R^2OCCHRCH_2SnX_3 \end{array}$$ Formula 6 or mixtures thereof, are obtained.

7. The process, as in claim 6 wherein the reaction of an ester of unsaturated carboxylic of the formula $R^1O-COCR=CH_2$ with metallic tin and an alcohol of the formula $R^2OH$ occurs in organic solvent.

8. The process, as in claim 6 wherein the reaction of the compounds resulting from the reaction an ester of unsaturated carboxylic of the formula $R^1O-COCR=CH_2$ with metallic tin and an alcohol of the formula $R^2OH$ occurring in organic solvent, and a compound selected from the formulas 1, 2 and 3 or mixtures thereof, are subjected to distillation to distill off the lower boiling alcohols, and solvent, before the mixture is further reacted with a compound of the formula $HSCH_{2m}COOR^2$.

9. The process, as in claim 6 wherein the reaction of the compound of the formula $HSCH_{2m}COOR^2$ L and the compound of the formula $HSR^2$ L and compound of the formula $HO-COR^2$ L or $HOCOCH=CHCOOR^2$ occurs in an organic solvent.

10. The process as in claim 6 wherein the organic solvent used is the same as that used in an earlier stage of the process.

11. A compound of the formula 1, $$\begin{array}{c} (R^1OCCHRCH_2)_n \\ \parallel \\ O \end{array} \diagdown SnCl_2 \diagup \begin{array}{c} (R^2OCCHRCH_2)_{2-n} \\ \parallel \\ O \end{array}$$ Formula 1 wherein R is a hydrogen atom or an alkyl group with 1–18 carbon atoms, $R^1$ is an alkyl group with 1–4 carbon atoms, $R^2$ is an alkyl group with 1–18 carbon atoms, and "n" value is 1, and $R^1$ and $R^2$ alkyl groups in substituents $R^1OCOCHRCH_2$ and $R^2OCOCHRCH_2$ bonded with tin are different.

12. A compound of the formula 4, $$\begin{array}{c} (R^1OCCHRCH_2)_n \\ \parallel \\ O \end{array} \diagdown SnX_2 \diagup \begin{array}{c} (R^2OCCHRCH_2)_{2-n} \\ \parallel \\ O \end{array}$$ Formula 4 wherein R is a hydrogen atom or an alkyl group with 1–18 carbon atoms, $R^1$ is an alkyl group with 1–4 carbon atoms, $R^2$ is an alkyl group with 1–18 carbon atoms, "n" is 1 and X is a group of the formula $SCH_{2m}COOR^2$, $SR^2mOCOR^2$ or $OCOCH=CHCOOR^2$, wherein "m"

is 1 or 2 and $R^2$ has the above specified meaning and $R^1$ and $R^2$ alkyl groups in substituents $R^1OCOCHRCH_2$ and $R^2OCOCHRCH_2$ bonded with tin are different.

13. A composition comprising mixtures of compounds of the formula 1

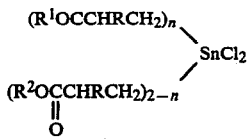
Formula 1 wherein R is a hydrogen atom or an alkyl group with 1–18 carbon atoms, $R^1$ is an alkyl group with 1–4 carbon atoms, $R^2$ is an alkyl group with 1–18 carbon atoms, and "n" value is 1, and $R^1$ and $R^2$ alkyl groups in substituents $R^1OCOCHRCH_2$ and $R^2OCOCHRCH_2$ bonded with tin are different.

14. A composition comprising mixtures of compounds of the formula 4

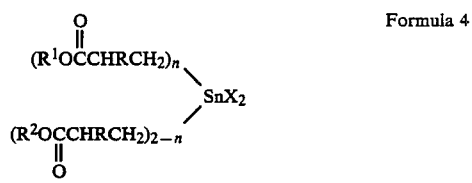
Formula 4 wherein R is a hydrogen atom or an alkyl group with 1–18 carbon atoms, $R^1$ is an alkyl group with 1–4 carbon atoms, $R^2$ is an alkyl group with 1–18 carbon atoms, "n" is 1 and X is a group of the formula $SCH_{2m}COOR^2$, $SR^2$, $OCOR^2$ or $OCOCH=CHCOOR^2$, wherein "m" is 1 or 2 and $R^2$ has the above specified meaning and $R^1$ and $R^2$ alkyl groups in substituents $R^1OCOCHRCH_2$ and $R^2OCOCHRCH_2$ bonded with tin are different.

15. The process, as in claim 4 wherein the mixture comprises $CH_3OCH_2CH_2$, $SnCl_3$, $C_4H_9OCOCH_2CH_2SnCl_3$, $[CH_3OCOCH_2CH_2]_2SnCl_2$, $[CH_2OCOCH_2CH_2]$ $[C_4H_8OCOCH_2CH_2]SnCl_2$, and $[C_4H_9OCOCH_2]_2SnCl_2$.

* * * * *